United States Patent [19]

Sullivan

[11] Patent Number: 5,591,135
[45] Date of Patent: Jan. 7, 1997

[54] SYRINGE STROKE CONTROLLER WITH ELASTICALLY ENABLED SINGLE AXIS SLIDE ADJUSTMENT AND FINGER-MOLDED PISTOL GRIP

[76] Inventor: James J. Sullivan, P.O. Box 1799, Ojai, Calif. 93024

[21] Appl. No.: 426,230

[22] Filed: Apr. 21, 1995

Related U.S. Application Data

[63] Continuation of Ser. No. 44,769, Apr. 12, 1993, abandoned.

[51] Int. Cl.⁶ .................................................. A61M 5/00
[52] U.S. Cl. ........................... 604/211; 604/208; 604/207
[58] Field of Search .......................... 604/207, 208, 604/211, 219, 220, 227, 183, 184, 131, 142, 181, 187, 200, 223, 257, 415, 905, 410, 61, 70, 72, 134, 135, 224; 606/190, 192, 194, 115; 222/105, 175; 433/89, 90

[56] References Cited

U.S. PATENT DOCUMENTS

| | | | |
|---|---|---|---|
| 3,162,217 | 12/1964 | Poli, Jr. et al. | 604/211 X |
| 4,033,346 | 7/1977 | Phillips et al. | 604/223 X |
| 4,204,539 | 5/1980 | Van Brugge | 604/195 X |
| 4,244,366 | 1/1981 | Raines | 604/211 |
| 4,479,781 | 10/1984 | Herold et al. | 433/90 |
| 4,968,303 | 11/1990 | Clarke et al. | 604/187 |

*Primary Examiner*—Randall L. Green
*Assistant Examiner*—V. Alexander
*Attorney, Agent, or Firm*—Michaelson & Wallace

[57] ABSTRACT

A stroke length regulating apparatus for use with plunging dispensers such as syringes includes a device for compressing the plunging dispenser consisting of a pair of supports movable relative to one another, a device for arresting relative displacement of the pair of supports at a selected end point which includes a threaded metering rod fixed near one end thereof to one of the supports, an elastically deformable nut having internal threads threadably engagable with the threaded metering rod along the length thereof, and a device for permitting temporary elastic deformation of the elastic deformable nut so as to disengage threads on the elastically deformable nut from threads on the metering rod, whereby to permit free movement of tile pair of supports relative to one another for stroke length adjustment of the dispenser.

30 Claims, 2 Drawing Sheets

SYRINGE STROKE CONTROLLER WITH ELASTICALLY ENABLED SINGLE AXIS SLIDE ADJUSTMENT AND FINGER-MOLDED PISTOL GRIP

This is a continuation of application Ser. No. 08/044,769, filed Apr. 12, 1993, now abandoned.

BACKGROUND OF THE INVENTION

1. Technical Field

The invention is related to adjustable stroke controlling mechanisms of the type employed to regulate or set the stroke length of a syringe in order to dispense a prescribed amount of fluid with each stroke of the syringe.

2. Background Art

Mechanisms for regulating or setting the stroke of a syringe to a precise predetermined stroke length corresponding to a desired amount of fluid to be dispensed from the syringe are well-known in the art. U.S. Pat. No. 4,244,366 discloses such a mechanism attached to a syringe and which is adjusted by rotating a threaded metering rod 10 of the mechanism at a knurled adjusting knob 12, as shown in FIG. 1 hereof. Rotation in one direction of the knob 12 lengthens the syringe stroke while rotation in the opposite direction reduces the stroke.

One problem with such a mechanism is that the adjustment from one stroke length to another is tedious and time-consuming, because tile user must rotate the knob 12 many times before the stroke length changes by any appreciable extent, depending upon the pitch of the threads in the metering rod 10. This latter problem is addressed in the above-mentioned U.S. Pat. No. 4,244,366 by providing a threaded nut 14 in fixed position relative to the syringe and engaging the threaded end of the metering rod 10 as shown in FIG. 2 hereof, the nut having a threaded passage 16 and a wider unthreaded passage 18 which opens into the threaded passage 16 through an intermediate opening 20 therebetween of a width sufficient to permit the metering rod 10 to squeeze through with application of some force. Whenever it is desired to quickly make a large adjustment in stroke length, the user forces the metering rod 10 out of the threaded passage 16 through the intermediate opening 20 therebetween and into the unthreaded passage 18. Once in the unthreaded passage, the metering rod 10 slides freely in the longitudinal direction for quick adjustment. Once the metering rod has been moved longitudinally to the desired position, the user forces it back into the threaded portion 16, at which it is held in place by engagement of the threads, permitting some fine adjustment by the user rotating the metering rod 10.

While the foregoing technique of U.S. Pat. No. 4,244,366 permits quicker adjustment of syringe stroke length compared with previous techniques, it has a number of significant problems. Foremost among such problems is that the opening 20 between the threaded and unthreaded passages 16, 18 in the nut 14 must be precisely formed so that it is just large enough so as to not require an undue amount of force to remove or return the metering rod to or from the threaded passage 16, but not so large as to permit the metering rod to inadvertently slip out of the threaded passage 16 at some inopportune moment. Thus, depending upon the precision of manufacture and the wearing of materials over long periods of use, the metering rod 10 might slip through the passage 20.

Another problem with the foregoing is that the required force to dislodge the metering rod from the threaded hole 16 is transverse and as such requires an awkward motion by the user. Moreover, it is a relatively violent motion, increasing the stress and fatigue involved in using such a device.

Accordingly, it is an object of the invention to provide a stroke setting mechanism which is smoothly adjustable using only a small amount of force and requiring no net transverse force across the metering rod and no violent movements or "popping" in or out of a mechanism or rod, so as to minimize fatigue and stress in the user.

It is a further object of the invention to provide a positive guard against slippage of the metering rod from its position set by the user, whereby the mechanism does not require extremely precise tolerances and is not affected by wear of materials over long periods of use.

It is a still further object of the invention to further minimize fatigue by permitting the strength of the entire hand to be employed in plunging the syringe without slippage of finger position on the apparatus.

These and other objects and benefits of the invention will become apparent in the description that follows when taken in conjunction with the drawings.

SUMMARY OF THE DISCLOSURE

The invention is a syringe stroke adjusting mechanism in which the metering rod is threaded into an internally threaded elastically deformable member threadably engaged to the metering rod at a selected longitudinal position. Whenever it is desired to quickly adjust the syringe stroke length by a relatively large change in stroke length, the user simply squeezes the internally threaded elastically deformable member to displace the internal threads thereof away from the metering rod threads, permitting unhindered longitudinal motion of the metering rod through the elastic member. This permits the user to change the fixed position of the elastically deformable member. Once the desired position is attained, the user stops squeezing the elastically deformable member, and the internal threads thereof reengage the metering rod threads to immediately fix the metering rod position. Fine adjustments are made by then rotating the elastically deformable member. The elastically deformable member has an elastically deformable locking cap providing a positive guard against inadvertent disengagement of the elastically deformable member from the metering rod. The movements required of the user are smooth and consistent with the use of a syringe, greatly minimizing user fatigue and stress over many uses.

In a preferred embodiment, the elastically deformable member is located at the end of the metering rod near the base or rear of the syringe, and its position on the metering rod determines the maximum distance that the syringe plunger may be pulled out, thus fixing the syringe dosage amount.

In a preferred embodiment, the elastically deformable member consists of a section of elastic leaves forming an internally threaded section engagable with and substantially surrounding the external threads of the metering rod at one end. The leaves are elastically biased away from the metering rod. The elastic locking cap has an inner cylinder with a ledge nestable in corresponding recesses in the outer surfaces of the elastic leaves, squeezing the leaves in upon the metering rod whenever the ledge is so nested. An outer cylinder of the locking cap concentric with the inner cylinder is attached thereto at base ends of both cylinders. The metering rod is released by the user squeezing the outer cylinder, which withdraws the ledge from the recesses and permits the locking cap to slide longitudinally off of the elastic leaves so as to no longer squeeze them onto the metering rod. To fix the position of the elastically deformable member on the metering rod, the user again squeezes the outer cylinder of the locking cap, and slides the locking cap longitudinally over the threaded leaves until the ledge engages the recesses.

Preferably, longitudinal movement of the locking cap is restricted in both directions between a position in which the metering rod is locked in position due to threadable engagement with the elastic leaves' threads and a position in which it is freely longitudinally slidable.

In accordance with a related aspect of the invention, the syringe holding mechanism is a V-shaped pistol grip mechanism hinged at the apex of the V. The syringe is held near the two ends of the V, and the legs thereof are sufficiently long to permit the user to wrap his entire hand thereabout. This permits the user to apply the strength of his entire hand to squeezing the syringe and driving the plunger thereof. In order to prevent slippage of the user's hand on the V-shaped holding mechanism, the outer edge of one of the legs of the V-shaped mechanism nearest the front end of the syringe includes finger recesses or grips while the outer edge of the opposite leg includes a recess to catch the corner in the user's hand between the thumb and index finger. The resultant prevention of hand slippage greatly reduces user fatigue and increases sureness of handling and safety.

DETAILED DESCRIPTION OF THE PREFERRED EMBODIMENTS

Figure 1:
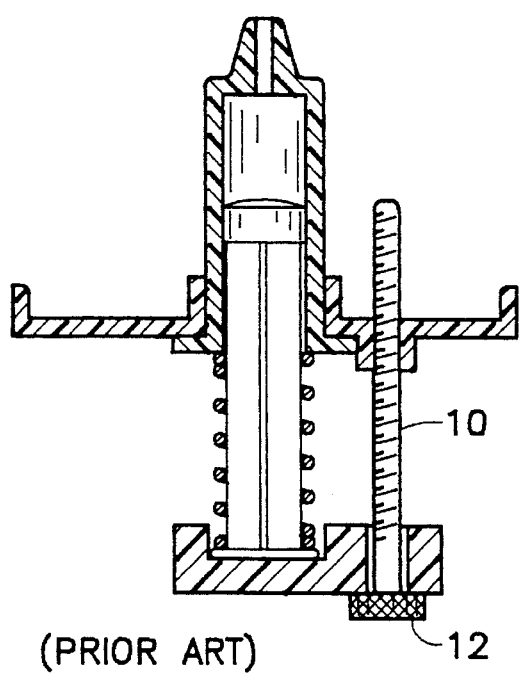
FIG. 1 is an elevational view of a syringe metering mechanism of the prior art.
Figure 2:
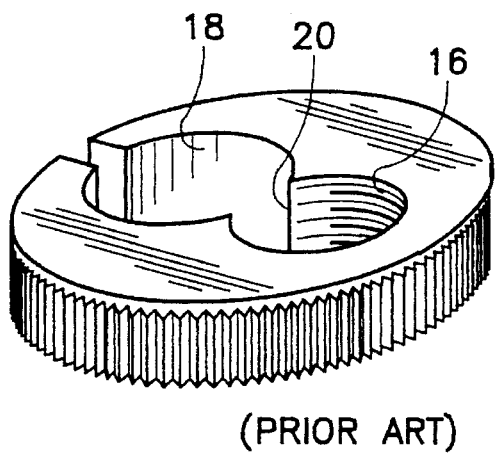
FIG. 2 is a perspective view of a metering rod nut of the prior art employed in the mechanism of FIG. 1.
Figure 3:
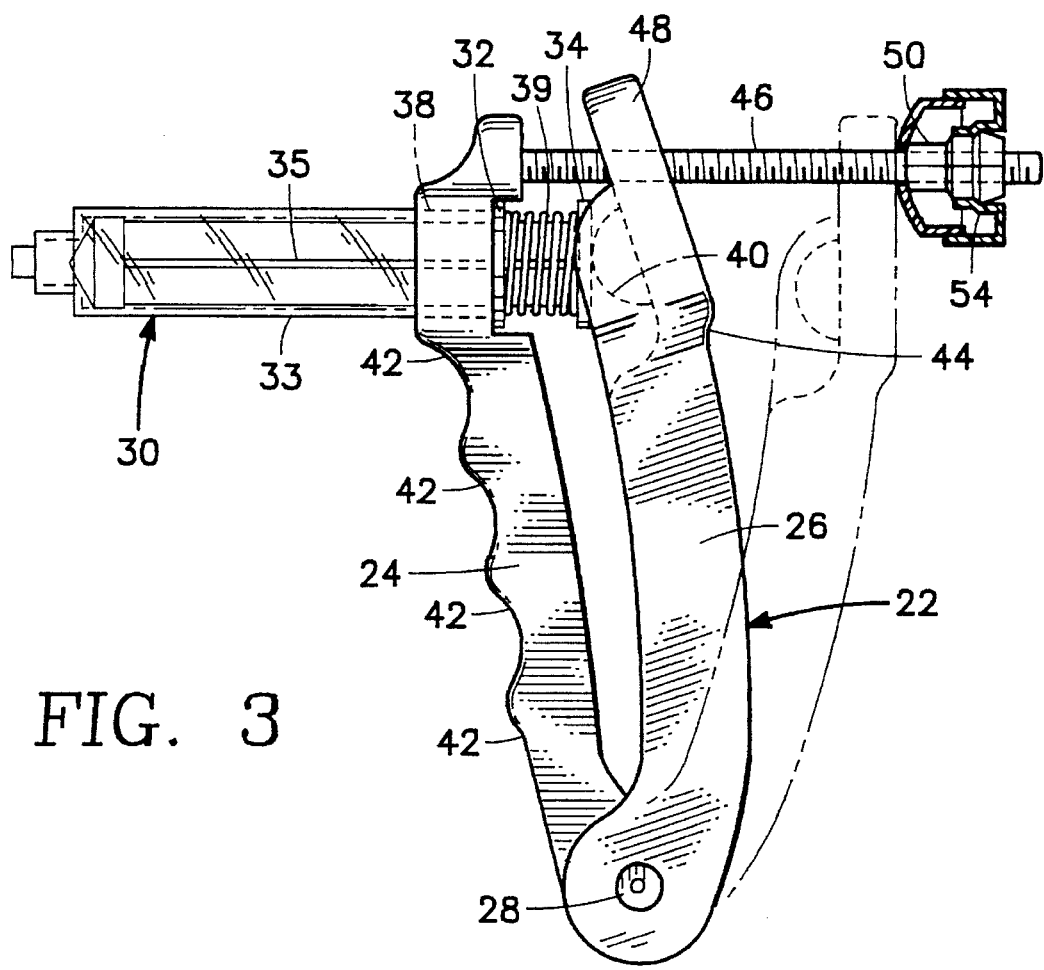
FIG. 3 is an elevational view of the pistol grip syringe metering mechanism of the present invention in the plunged position.
Figure 4:
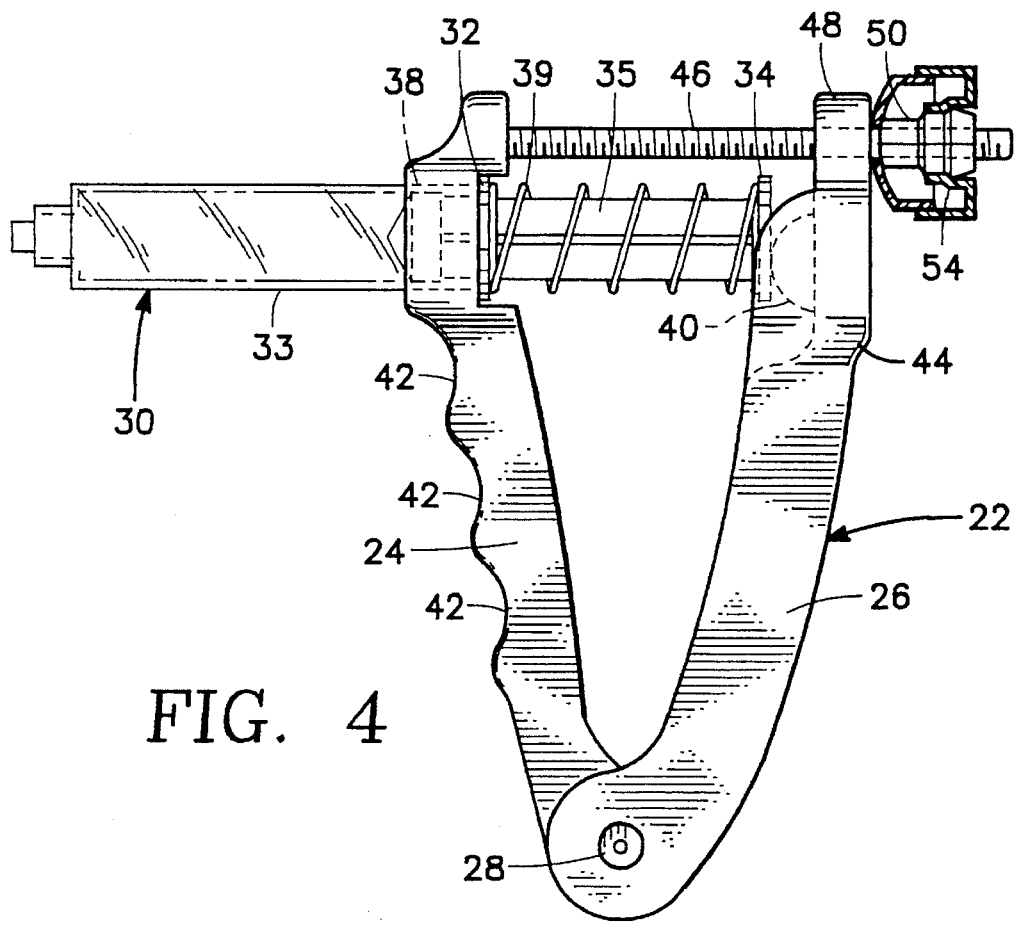
FIG. 4 is an elevational view of the pistol grip syringe metering mechanism of FIG. 3 in the withdrawn position.

Referring to FIG. 3, a V-shaped pistol-grip syringe holder 22 includes a pair of legs including a front leg 24 and a back leg 26 hinged together at a hinge joint 28. A syringe 30 is held near the ends of the legs 24, 26. The syringe 30 includes a forward flange 32 at the rear of the syringe's barrel 33 and a rear flange 34 at the base of the syringe's plunger 35. The syringe barrel 33 is inserted through a barrel-receiving hole 38 in the forward leg 24 until the forward flange 32 abuts a shoulder surrounding the hole 38. The rear leg 26 is moved toward the front leg 24 until a semi-spherical button 40 on the rear leg 26 abuts the rear flange 34. Further movement of the rear leg 26 toward the front leg 24 drives the plunger 35 into the barrel 33, compressing a spring 39 held between the two flanges 32, 34. Four finger grips or recesses in the front surface of the front leg 24 and a recess 44 in the back surface of the rear leg 26 for nesting the corner between the thumb and index finger provide sure control and minimization of user hand fatigue and greater ease of use. Releasing compressive force on the spring 39 permits the spring to withdraw the plunger 35 from the barrel 33 until the rear leg reaches an end-of-travel point relative to the front leg 24.

Figure 5:
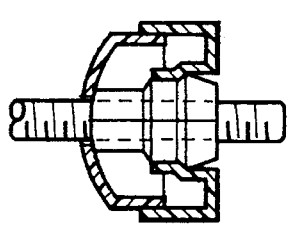
FIG. 5 is an elevational sectional view of the metering rod slip adjustment device of the present invention in the locked position.
Figure 8:
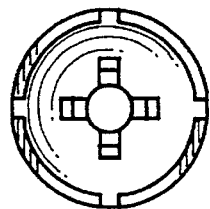
FIG. 8 is an end view corresponding to FIG. 7.
Figure 9:
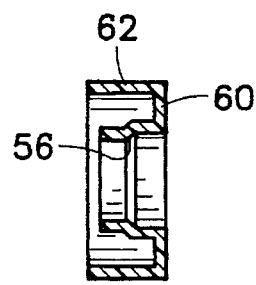
FIG. 9 is an elevational sectional view of the locking cap of the elastically locking slip adjustment device of FIG. 5.
Figure 10:
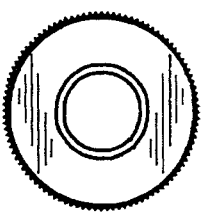
FIG. 10 is an end view corresponding to FIG. 9.

This end-of-travel point is selected by the user in order to precisely fix the amount of liquid dispensed from the syringe 30 during the next time the plunger 35 is driven to the end of the barrel 33. For this purpose, a cylindrical metering rod 46 having a threaded outer surface is fastened at its forward end to the end of the forward leg 24 and extends near its other end through an unthreaded hole 48 in the end of the rear leg 26. The metering rod 46 is parallel with the axis of the syringe barrel 33 and plunger 35. The metering rod 46 is threaded through internal threads of an elastic nut 50 (FIGS. 7 and 8) consisting of plural elastically deformable leaves 52 surrounding the metering rod 46, the surfaces of the leaves 52 facing the rod 46 being threaded to provide the internal threads of the nut 50 (FIG. 5). In the absence of other forces, the leaves 52 are elastically biased to spring away from the metering rod 46. In order to compress the leaves 52 onto the metering rod and securely engage the threads thereof, an elastically deformable locking cap 54 (FIGS. 9 and 10) surrounds and compresses the leaves 52 so as to force the inwardly facing threads of the leaves 52 to engage the outwardly facing threads of the metering rod 46 (FIG. 5).

In order to prevent the locking cap 54 from inadvertently sliding off the leaves 52 or locking nut 50, the locking cap 54 includes an internal cylindrical surface having a radially inwardly protruding ledge which nestably locks into matching recesses 58 in the outer surface of the leaves 52.

In order to permit unlocking the cap 54 from the leaves 52 for disengagement of the leaves 52 from the rod 46, the cylindrical locking cap 54 is formed with an annulus 60 with an outer cylindrical knob 62 formed about the outer circumference of the annulus 60. Preferably, the outer surface of the knob 62 is knurled. By squeezing the knob 62, the user elastically deforms the locking cap 54, causing tile ledge 56 to withdraw from the recesses 58. This permits the user to freely move the legs 24, 26 relative to one another for large quick adjustments of the syringe starting position and dispensing amount. Once the desired position is reached, the user relaxes the knob, and the leaves 52 again compress against the rod 46, fixing the end-of-travel position. Further fine adjustment of rod position/syringe dispensing amount is attained by rotating the nut 50 or (in an alternative embodiment) by rotating the rod 46.

Figure 6:
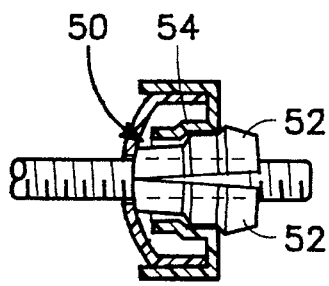
FIG. 6 is an elevational view corresponding to that of FIG. 5, but showing the unlocked position.
Figure 7:
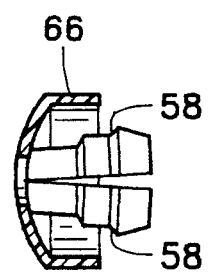
FIG. 7 is an elevational sectional view of the internally threaded section of the slip adjustment device of FIG. 5.

In order to permit the rod position to remain freely adjustable without continuing to compress the knob 62, the user, while compressing the knob 62, may slide the locking cap assembly 54, 60, 62 toward the rear leg 26 until the ledge 56 is no longer registered with the recesses 58, attaining the configuration illustrated in FIG. 6. At this point, the user may release the knob 62, while the rod position remains freely adjustable by squeezing or opening the V-shaped mechanism 22. To lock the rod position, the user slides the locking cap assembly 54, 60, 62 in the opposite direction until the ledge 56 snaps back into the recesses 58 to attain the configuration of FIG. 5. In order to facilitate this motion with a minimum of force, the outer surface of the assembly of leaves 52 opens gradually to a larger radius until a maximum radius is reached adjacent the recesses 58, providing a partial conical cross-section surface as shown in FIG. 7.

In order to restrict the movement of the locking cap 54 relative to the nut 50 from its locked position illustrated in FIG. 5 to its unlocked position illustrated in FIG. 6, the locking nut 50 includes an annular section formed with an outer cylindrical section 66. As the locking nut is moved from the position of FIG. 5 to the position of FIG. 6, its motion is stopped when the cylindrical section 66 of the nut 50 abuts the annulus 60 of the locking cap 54. Thus, the user readily moves the locking cap between position 0f FIG. 5 in which the ledge 56 is engaged with the recesses 58 and the position of FIG. 6 in which the conical shape of the leaves 54 biases the cylinder 66 against the annulus 60. Thus, the locking cap position is stable in both the configurations of FIGS. 5 and 6.

While the invention has been described in detail by specific reference to preferred embodiments, it is understood that variations and modifications thereof may be made without departing from the true spirit and scope of the invention.

What is claimed is:

1. A stroke length regulating apparatus for use with a syringe-like dispenser, the dispenser having a barrel portion and a plunger portion, the apparatus comprising:

means for compressing the dispenser comprising a pair of interconnected supports movable relative to one another, one of said supports coupled to the barrel portion of the dispenser and the other of said supports coupled to the plunger portion of the dispenser;

means for arresting relative displacement of said pair of supports at a selected end point, comprising:

a threaded metering rod having a longitudinal axis of symmetry and fixed at one end thereof to a first one of said supports; and a dual-mode elastically deformable rotatable nut comprising, means for threadably engaging said threaded metering rod along a length thereof comprising a cylinder around said metering rod and plural elastically deformable leaves extending axially from an edge of said cylinder and surrounding a portion of said metering rod, wherein said leaves have threads facing and engagable with threads on said metering rod, wherein once engaged said engaging means facilitates longitudinal displacement along said rod by rotation of said nut about a rotational axis thereof in a first mode of said nut, and wherein said engaging means enables said elastically deformable nut to prevent movement of a second one of said supports away from the first one of said supports past said selected endpoint, and means for permitting temporary elastic deformation of said elastic deformable nut so as to withdraw said engaging means away from threads on said metering rod and thereby permit free movement of said pair of supports relative to one another for stroke length adjustment of the dispenser in a second mode of said nut, said rod constraining said nut so as to maintain said rotational axis generally coincident with the longitudinal axis in both said first and second mode, and wherein said permitting means comprises an elastically deformable locking cap comprising a cylinder portion around said leaves urging said leaves toward said metering rod whereby to engage the threads thereof and means for deforming said locking cap whereby to withdraw said cylinder portion away from said leaves.

2. The apparatus of claim 1 wherein said leaves are elastically biased away from said metering rod.

3. The apparatus of claim 1 wherein said elastically deformable locking cap further comprising means for preventing inadvertent movement of said cylinder portion and disengagement of said leaves from said metering rod.

4. The apparatus of claim 3 wherein said means for preventing inadvertent movement comprises a ledge in said cylinder portion facing said leaves and a recess in each of said leaves matching said ledge and in which said ledge is nestable.

5. The apparatus of claim 4 wherein said locking cap and cylinder portion thereof are axially displaceable along said leaves, whereby to permit disengagement of the threads of said rod and leaves without deformation of said elastically deformable nut.

6. The apparatus of claim 5 wherein said leaves present a conical outer surface to said cylinder portion of said locking cap of maximum radius near said recesses, whereby said cylinder portion is urged away from said recesses after disengagement of said ledge therefrom.

7. The apparatus of claim 6 further comprising means for limiting axial movement of said locking cap, cylinder portion and ledge thereof relative to said leaves.

8. The apparatus of claim 7 wherein said means for deforming said locking cap comprises an annulus extending outwardly from said cylinder portion of said locking cap and an outer cylindrical knob formed at the periphery of said annulus.

9. The apparatus of claim 8 wherein:

said means for limiting axial movement comprise an annular section formed on the cylinder of said nut from which said leaves extend axially, and an outer cylinder on the periphery of said annular section extending toward said annulus of said locking cap and abutting therewith upon said locking cap reaching a maximum axial displacement.

10. The apparatus of claim 1 wherein said pair of interconnected supports comprise a pair of arms hinged together at facing ends thereof and engaged with the dispenser at opposite ends thereof, at least one of said arms having finger grips formed therein.

11. The apparatus of claim 10 wherein the other one of said arms has a recess for catching a palm of a user's hand.

12. The apparatus of claim 11 wherein said one arm is adjacent a front end of the dispenser and said other arm is adjacent a rear end of the dispenser, whereby to provide a pistol grip.

13. A stroke length regulating apparatus for use with a syringe-like dispenser, the dispenser having a barrel portion and a plunger portion, the apparatus comprising:

means for compressing the dispenser comprising a pair of interconnected supports movable relative to one another, one of said supports coupled to the barrel portion of the dispenser and the other of said supports coupled to the plunger portion of the dispenser;

means for arresting relative displacement of said pair of supports at a selected end point, comprising:

a threaded metering rod having a longitudinal axis of symmetry and fixed at one end thereof to a first one of said supports; and a dual-mode elastically deformable rotatable nut comprising, means for threadably engaging said threaded metering rod along a length thereof comprising a cylinder around said metering rod and plural elastically deformable leaves extending axially from an edge of said cylinder and surrounding a portion of said metering rod, wherein said leaves have threads facing and engagable with threads on said metering rod, wherein once engaged said engaging means facilitates longitudinal displacement along said rod by rotation of said nut about a rotational axis thereof in a first mode of said nut, and wherein said engaging means enables said elastically deformable nut to prevent movement of a second one of said supports away from the first one of said supports past said selected endpoint, and means for radially expanding a portion of said elastic deformable nut in response to a squeezing of said elastically deformable nut by a user so as to withdraw said engaging means from threads on said metering rod and thereby permit free movement of said pair of supports relative to one another for stroke length adjustment of the dispenser in a second mode of said nut, said rod constraining said nut so as to maintain said rotational axis generally coincident with the longitudinal axis in both said first mode and said second mode, and wherein said radially expanding means comprises an elastically deformable locking cap comprising a cylinder portion around said leaves urging said leaves toward said metering rod whereby to engage the threads thereof and means for deforming said locking cap whereby to withdraw said cylinder portion away from said leaves.

14. The apparatus of claim 13 wherein said leaves are elastically biased away from said metering rod.

15. The apparatus of claim 13 wherein said locking cap and cylinder portion thereof are axially displaceable along said leaves, whereby to permit disengagement of the threads of said rod and leaves without deformation of said elastically deformable nut.

16. A stroke length regulating apparatus for use with a syringe-like dispenser, the dispenser having a barrel portion and a plunger portion, the apparatus comprising:

means for compressing the dispenser comprising a pair of interconnected supports movable relative to one another, one of said supports coupled to the barrel portion of the dispenser and the other of said supports coupled to the plunger portion of the dispenser;

means for arresting relative displacement of said pair of supports at a selected end point, comprising:

a threaded metering rod fixed at one end thereof to a first one of said supports; and an elastically deformable nut comprising, means for threadably engaging said threaded metering rod along a length thereof comprising a cylinder around said metering rod and plural elastically deformable leaves extending axially from an edge of said cylinder and surrounding a portion of said metering rod, wherein said leaves have threads facing and engagable with threads on said metering rod, and wherein said engaging means enables said elastically deformable nut to prevent movement of a second one of said supports away from the first one of said supports past said selected endpoint, and means for permitting temporary elastic deformation of said elastic deformable nut so as to withdraw said engaging means away from threads on said metering rod and thereby permit free movement of said pair of supports relative to one another for stroke length adjustment of the dispenser, said permitting means comprising an elastically deformable locking cap comprising a cylinder portion around said leaves urging said leaves toward said metering rod whereby to engage the threads thereof and means for deforming said locking cap whereby to withdraw said cylinder portion away from said leaves.

17. The apparatus of claim 16 wherein said leaves are elastically biased away from said metering rod.

18. The apparatus of claim 16 wherein said elastically deformable locking cap further comprising means for preventing inadvertent movement of said cylinder portion and disengagement of said leaves from said metering rod.

19. The apparatus of claim 18 wherein said means for preventing inadvertent movement comprises a ledge in said cylinder portion facing said leaves and a recess in each of said leaves matching said ledge and in which said ledge is nestable.

20. The apparatus of claim 19 wherein said locking cap and cylinder portion thereof are axially displaceable along said leaves, whereby to permit disengagement of the threads of said rod and leaves without deformation of said elastically deformable nut.

21. The apparatus of claim 20 wherein said leaves present a conical outer surface to said cylinder portion of said locking cap of maximum radius near said recesses, whereby said cylinder portion is urged away from said recesses after disengagement of said ledge therefrom.

22. The apparatus of claim 21 further comprising means for limiting axial movement of said locking cap, cylinder portion and ledge thereof relative to said leaves.

23. The apparatus of claim 22 wherein said means for deforming said locking cap comprises an annulus extending outwardly from said cylinder portion of said locking cap and an outer cylindrical knob formed at the periphery of said annulus.

24. The apparatus of claim 23 wherein:

said means for limiting axial movement comprise an annular section formed on the cylinder of said nut from which said leaves extend axially, and an outer cylinder on the periphery of said annular section extending toward said annulus of said locking cap and abutting therewith upon said locking cap reaching a maximum axial displacement.

25. The apparatus of claim 16 wherein said pair of interconnected supports comprise a pair of arms hinged together at facing ends thereof and engaged with the dispenser at opposite ends thereof, at least one of said arms having finger grips formed therein.

26. The apparatus of claim 25 wherein the other one of said arms has a recess for catching a palm of a user's hand.

27. The apparatus of claim 26 wherein said one arm is adjacent a front end of the dispenser and said other arm is adjacent a rear end of the dispenser, whereby to provide a pistol grip.

28. A stroke length regulating apparatus for use with a syringe-like dispenser, the dispenser having a barrel portion and a plunger portion, the apparatus comprising:

means for compressing the dispenser comprising a pair of interconnected supports movable relative to one another, one of said supports coupled to the barrel portion of the dispenser and the other of said supports coupled to the plunger portion of the dispenser;

means for arresting relative displacement of said pair of supports at a selected end point, comprising:

a threaded metering rod fixed at one end thereof to a first one of said supports; and an elastically deformable nut comprising, means for threadably engaging said threaded metering rod along the length thereof comprising a cylinder around said metering rod and plural elastically deformable leaves extending axially from an edge of said cylinder and surrounding a portion of said metering rod, wherein said leaves have threads facing and engagable with threads on said metering rod, and wherein, said engaging means enables said elastically deformable nut to prevent movement of a second one of said supports away from the first one of said supports past said selected endpoint, and means for radially expanding a portion of said elastic deformable nut so as to withdraw said engaging means from threads on said metering rod and thereby permit free movement of said pair of supports relative to one another for stroke length adjustment of the dispenser, said radially expanding means comprising an elastically deformable locking cap comprising a cylinder portion around said leaves urging said leaves toward said metering rod whereby to engage the threads thereof and means for deforming said locking cap whereby to withdraw said cylinder portion away from said leaves.

29. The apparatus of claim 28 wherein said leaves are elastically biased away from said metering rod.

30. The apparatus of claim 28 wherein said locking cap and cylinder portion thereof are axially displaceable along said leaves, whereby to permit disengagement of the threads of said rod and leaves without deformation of said elastically deformable nut.

* * * * *